June 7, 1955 R. L. BYRUM Plant Pat. 1,397
ROSE PLANT
Filed Oct. 11, 1954
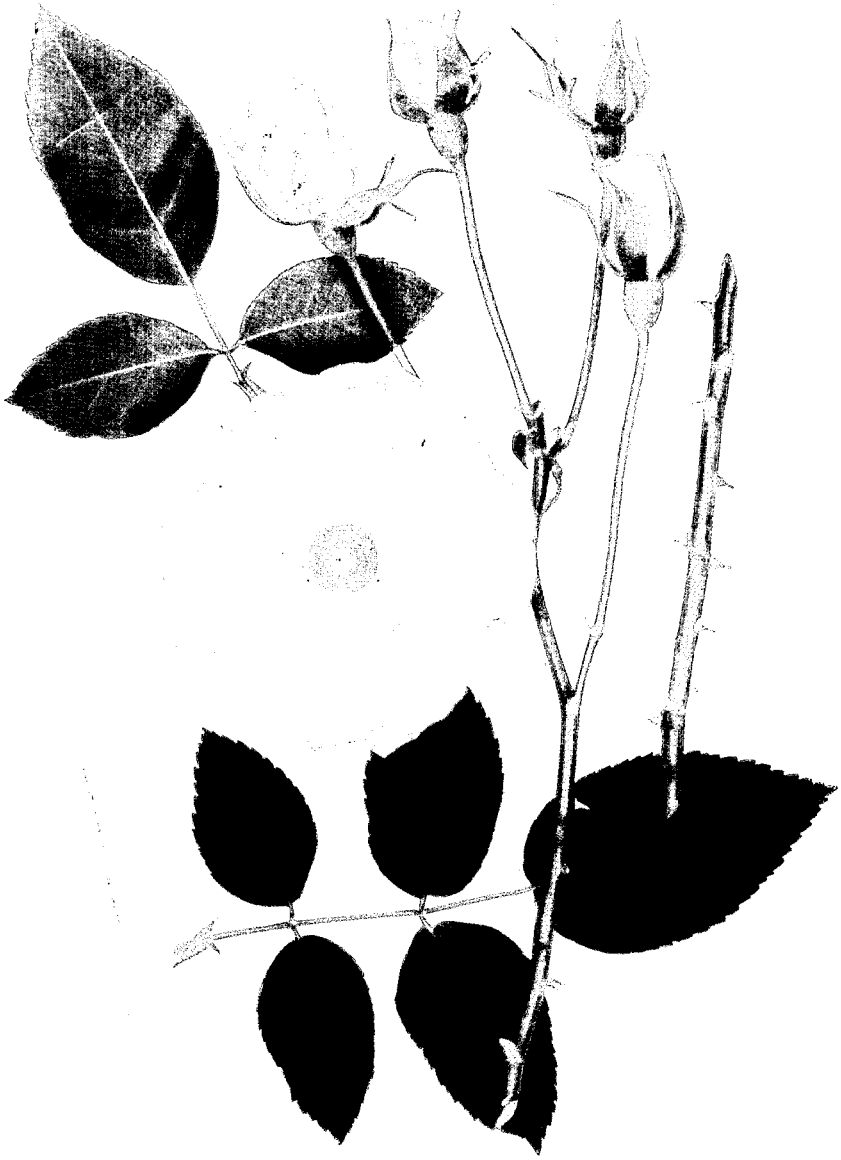
Inventor.
R. L. Byrum
By: Robb & Robb
Attorneys.

United States Patent Office

Plant Pat. 1,397

Patented June 7, 1955

1,397

ROSE PLANT

Roy L. Byrum, Richmond, Ind., assignor to Joseph H. Hill Company, Richmond, Ind., a corporation of Indiana Application October 11, 1954, Serial No. 461,702

1 Claim. (Cl. 47—61)

The present invention relates to a new and distinct variety of rose plant of the polyantha class, which was originated by me by crossing the variety "Garnette" (unpatented) with the variety "Pink Bountiful" (Plant Patent No. 601).

The primary objective in making this cross was to endeavor to combine the unusually good keeping qualities of the variety "Garnette" with the good cut flower forcing qualities under glass of the variety "Pink Bountiful." This objective was fully achieved, as evidenced by the fact that my new variety has keeping qualities comparable to "Garnette," while at the same time clustering more than that variety and bearing flowers of a different color and type, as well as being better adapted to forcing under glass in winter while other varieties tend to go dormant. Although the parent variety "Pink Bountiful" clusters when grown out-of-doors, it produces only one bloom per stem when grown in greenhouses, whereas my new variety clusters well in the greenhouse, and the clusters develop more uniformly.

My new variety more nearly resembles the variety "Pink Rosette" (Plant Patent No. 902) than any other variety, but is definitely differentiated from the latter by its ability to continue to produce blooms in winter while "Pink Rosette" tends to go dormant in greenhouses, and the new variety is a better keeper, has better bud and cluster form and better stems than "Pink Rosette."

These various features of my new variety, as aforementioned, definitely distinguish the same from its parents, as well as from all other varieties of which I am aware, and asexual reproduction of my new variety by grafting as performed at Richmond, Indiana, and by budding as performed at Wills Point, Texas, shows that these characteristics and distinctions come true to form and are established and transmitted through succeeding propagations.

The accompanying drawing shows typical specimens of the flowers, foliage and stems of my new variety in different stages of development, and as depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway"), Koster's Color Guide (hereinafter abberviated as "Koster"), and Robert F. Wilson's Horticultural Colour Chart (hereinafter abbreviated as "Wilson"), as indicated:

Type: Greenhouse; bush; seedling.
Class: Polyantha.
Breeding: Seedling.
*Seed parent.*—"Garnette."
*Pollen parent.*—"Pink Bountiful."
Propagation: Holds its distinguishing characteristics through succeeding propagations by both grafting and budding.

FLOWER

Locality where grown and observed: Richmond, Indiana, and Wills Point, Texas.
Flowers borne: Several to stem; in clusters; on medium length stems of medium strength.
Quantity of bloom: Free.
Continuity: Continuous.
Fragrance: Slight. Nature—spicy.
Bud:
*Peduncle.*—Medium length; small diameter; erect; medium strength. Bark — smooth. Color—Scheele's Green, Plate 860/2 (Wilson). Thorns—none. Prickles — none. Hairs — numerous. Color—Pure White, Plate 1 (Koster).
*Before calyx breaks.*—Size—small. Form—short pointed; ovoid; with a conspicuous neck; with foliaceous appendages on the surface of the bud; with slender, entire foliaceous parts extending beyond the tip of the bud equal to ¼ or more of its length. Color—Scheele's Green, Plate 860/1 (Wilson).
*As calyx breaks.*—Color (outside of petal)—Spiraea Red, Plate 025 (Wilson).
*As first petal opens.*—Size—medium small. Form—short pointed; ovoid. Color: Outside — Rose Madder, Plate 23/1 (Wilson). Inside—Neyron Rose, Plate 623/2 (Wilson); some parts overlaid with Neyron Rose, Plate 623/1 (Wilson).
*Opening.*—Opens up well in greenhouse; is affected normally by weather conditions, but without unusual characteristics.
Bloom:
*Size (when fully open).*—Small; from 2½ inches to 3 inches.
*Petalage.*—Double, but stamens not hidden; from 25 to 30 petals; arranged irregularly.
*Form.*—High-centered at first, but becoming flat-open; petals being at first tightly rolled outward, but becoming loosely rolled outward later at maturity.
Petals: Moderately thick. Inside — satiny; outside—satiny.
*Shape.*—Outside petals—obovate; apex mucronate. Intermediate petals—Obovate; apex mucronate. Inside petals—Obovate; apex mucronate.

This description of a newly opened flower was made from a rose grown in a greenhouse in the month of January at Richmond, Indiana:

Color:
*Outside petal.*—Outside surface—Phlox Pink, Plate 625/1 (Wilson), with base of petal Chartreuse Green, Plate 663/3 (Wilson). Inside surface—Phlox Pink, Plate 625/2 (Wilson), lightly pencilled with Phlox Pink, Plate 625/1 (Wilson); base of petal Chartreuse Green, Plate 663/3 (Wilson).
*Intermediate petal.*—Outside surface—Phlox Pink, Plate 625/1 (Wilson), with base of petal Chartreuse Green, Plate 663/3 (Wilson). Inside surface—Phlox Pink, Plate 625/3 (Wilson), overlaid very lightly with Phlox Pink, Plate 625/2 (Wilson); base of petal Chartreuse Green, Plate 663/3 (Wilson).
*Inner petal.*—Outside surface—Phlox Pink, Plate 625/1 (Wilson), with base of petal Chartreuse Green, Plate 663/3 (Wilson). Inside surface—Phlox Pink, Plate 625/3 (Wilson), overlaid very lightly with Phlox Pink, Plate 625/2 (Wilson); base of petal Chartreuse Green, Plate 663/3 (Wilson).

This description was made from a rose that was open for three days in a greenhouse in the month of June at Richmond, Indiana:

Color:

*Outside petal.*—Outside surface—Phlox Pink, Plate 625/2 (Wilson), with base of petal Chartreuse Green, Plate 663/3 (Wilson). Inside surface—Phlox Pink, Plate 625/3 (Wilson), lightly pencilled with Phlox Pink, Plate 625/2 (Wilson); base of petal Chartreuse Green, Plate 663/3 (Wilson).

*Intermediate petal.*—Outside surface—Phlox Pink, Plate 625/2 (Wilson), with base of petal Chartreuse Green, Plate 663/3 (Wilson). Inside surface—Phlox Pink, Plate 625/3 (Wilson), lightly pencilled with Phlox Pink, Plate 625/2 (Wilson); base of petal Chartreuse Green, Plate 663/3 (Wilson).

*Inner petal.*—Outside surface—Phlox Pink, Plate 625/3 (Wilson), with base of petal Chartreuse Green, Plate 663/3 (Wilson). Inside surface—Phlox Pink, Plate 625/3 (Wilson), overlaid very lightly with Phlox Pink, Plate 625/2 (Wilson); base of petal Chartreuse Green, Plate 663/3 (Wilson).

Behavior: Persist in greenhouse; affected normally by weather conditions, but without unusual characteristics; fades to Rose Pink, Plate 427/2 (Wilson).

Flower longevity: Cut roses grown in greenhouse and kept at living-room temperatures—4 or 5 days in January.

General color effect: Newly opened flower—from Phlox Pink, Plate 625/3 (Wilson) to Phlox Pink, Plate 625/2 (Wilson). 3-days open—Rose Pink, Plate 427/1 (Wilson).

PLANT

Foliage:

*Leaves.*—Compound of 3 to 5 leaflets; abundant; medium large; heavy; leathery.

*Leaflets.* — Shape — ovoid. Apex — acuminate. Base—round. Margin—simply serrate.

*Color.*—Mature: Upper surface—near Taxus Green, Plate 81 (Koster); under surface—near Pois Green, Plate XLI (Ridgway). Young: Upper surface—Pod Green, Plate 061/2 (Wilson), overlaid with Neutral Red, Plate XXXVIII (Ridgway); under surface—Pod Green, Plate 061/3 (Wilson), slightly overlaid with Neutral Red, Plate XXXVIII (Ridgway).

*Rachis (the supporting stem of the compound leaf).*—Light. Upper side—grooved; under side—prickly.

*Stipules.*—Moderately short; narrow; with moderately short points turning out at an angle of more than 45°.

Growth:

*Habit.*—Bush; upright; much-branched.

*Growth.*—Free; vigorous.

*Canes.*—Medium diameter.

*Main stems.*—Color—some Maroon, Plate 97 (Koster); some Cedar Green, Plate 80 (Koster); some Cedar Green, Plate 80 (Koster), overlaid with Maroon, Plate 97 (Koster). Thorns—several; medium length; hooked downward; with narrow, short base. Color—Red Ochre, Plate 94 (Koster). Prickles—few. Color—Red Ochre, Plate 94 (Koster). Hairs—none.

*Branches.*—Color—Spinach Green, Plate 0960/1 (Wilson). Thorns—several; medium length; hooked downward; with short, narrow base. Color—Light Russet-Vinaceous, Plate XXXIX (Ridgway). Prickles—few. Color—Light Russet-Vinaceous, Plate XXXIX (Ridgway). Hairs—none.

*New shoots.*—Color—Pod Green, Plate 061/2 (Wilson), partly overload with Neutral Red, Plate XXXVIII (Ridgway). Thorns— few; medium length; hooked downward; with short, narrow base. Color—Light Russet-Vinaceous, Plate XXXIX, (Ridgway). Prickles—none. Hairs—none.

REPRODUCTIVE ORGANS

Stamens: Many; arranged regularly about pistils.

Filaments: Medium length; most with anthers. Color—Chartreuse Green, Plate 663/3 (Wilson).

Anthers: Medium small; all open at once. Color—Maize Yellow, Plate 607/2 (Wilson).

Pollen: Abundant. Color—Yellow Ochre, Plate 07/2 (Wilson).

Pistils: Many.

Styles: Uneven; medium length; thin; loosely bunched. Color—Phlox Pink, Plate 625/3 (Wilson).

Stigma: Color—Pure White, Plate 1 (Koster).

Ovularies: Almost all encased in calyx, but few protruding.

Sepals: Permanent; medium length; straight; spear-shaped. Color: Inside—Scheele's Green, Plate 860 (Wilson), with white fuzz around edges and over the surface; outside—Scheele's Green, Plate 860 (Wilson), with white fuzz around edges.

I claim:

A new and distinct variety of rose plant of the polyantha class, substantially as herein shown and described, characterized particularly as to novelty by its good cut flower forcing qualities under glass, its good cluster flowering habit and uniformity of development of the clusters, its superior bud and cluster form and good stems, the superior keeping qualities of its flowers, and the distinctive Phlox Pink general color tonality of its flowers.

No references cited.